United States Patent [19]

Tischlinger

[11] 4,178,928

[45] * Dec. 18, 1979

[54] SELF INJECTOR

[76] Inventor: Edward A. Tischlinger, 7 Froghollow Rd., East Lyme, Conn. 06333

[*] Notice: The portion of the term of this patent subsequent to Feb. 7, 1995, has been disclaimed.

[21] Appl. No.: 823,419

[22] Filed: Aug. 10, 1977

[51] Int. Cl.² .............................................. A61M 5/20
[52] U.S. Cl. .................................. 128/215; 128/218 F
[58] Field of Search ............... 128/173 H, 215, 218 F, 128/218 FA, 218 A, 218 D, 218 NV, 234

[56] References Cited

U.S. PATENT DOCUMENTS

| | | | |
|---|---|---|---|
| 2,735,429 | 2/1956 | Huber | 128/218 NV |
| 3,308,821 | 3/1967 | Shields | 128/218 NV |
| 3,396,726 | 8/1968 | Sarnoff | 128/218 F |
| 3,742,948 | 7/1973 | Post et al. | 128/218 F |
| 4,031,893 | 6/1977 | Kaplan et al. | 128/218 F |
| 4,072,149 | 2/1978 | Tischlinger | 128/218 NV |

*Primary Examiner*—Dalton L. Truluck

*Attorney, Agent, or Firm*—Witherspoon, Lane & Hargest

[57] ABSTRACT

A self injector having a spring powered gun assembly including a plunger rod driven forwardly by a compressed spring which is releasable by a retainer member to fire the plunger rod, and a cartridge assembly connected to said gun assembly, the cartridge assembly comprising a cylindrical shield connected to the gun assembly, a cartridge slidably positioned within the shield and including a cartridge tube with a slidable plunger closing off one end and a flexible diaphragm closing off the other to form a medicament chamber therebetween. A nose piece is affixed to the diaphragm end of the cartridge tube and mounts a cannula on its outside portion in fluid communication with the area on the cannula side of the diaphragm. The plunger rod is aligned with the cartridge plunger whereby when the gun is fired the plunger rod will push the plunger forwardly in the cartridge tube to cause the flexible diaphragm to contact and be pierced by a spike in the cartridge tube thereby establishing fluid communication between the medicament chamber and the cannula for injection purposes.

8 Claims, 6 Drawing Figures

SELF INJECTOR

SUMMARY OF THE INVENTION

There is an ever increasing need for injectors of the self administration type. For example, persons with various medical problems relative to heart, diabetes and even allergies may now be provided with injection units which may be self administered particularly in times of emergency. Obviously, since such devices very often fall into a life saving category, it is imperative that the self injector must have good storage characteristics, must be simple to operate and virtually one hundred percent reliable.

In view of the foregoing it is an object of this invention to provide a self injector which is simple to operate and virtually foolproof.

It is another object of this invention to provide a self injector having excellent storage characteristics.

It is yet another object of this invention to provide a self injector adaptable for use with a wide range of medicaments.

It is a still further object of this invention to provide a self injector having a spring powered gun assembly for driving a plunger rod which engages a slidable plunger within a cartridge assembly to both insert the cannula and inject the medicament into the prescribed locus.

The above and additional objects and advantages will become more apparent when taken in conjunction with the following detailed description and drawings.

IN THE DRAWINGS

FIG. 1 is a sectional view of the self injector of this invention as it appears ready to use, FIG. 2 is a longitudinal view partly in section illustrating the position of the plunger rod and cannula shortly after release, FIG. 3 is a longitudinal view partly in section showing the cannula fully extended and the diaphragm pierced with the plunger piston forcing the medicament out the cannula, FIG. 4 is a plan view of the nose piece taken from the diaphragm side with the diaphragm removed to show the spike and area which receives the diaphragm, FIG. 5 is a cross sectional view taken along lines 5—5 of FIG. 1 illustrating the radially extending spike supports and the opening connecting the cannula with the diaphragm chamber, and FIG. 6 is a perspective view illustrating the release knob and the manner in which it cooperates with the rear portion of the plunger rod.

DETAILED DESCRIPTION

Figure 1:
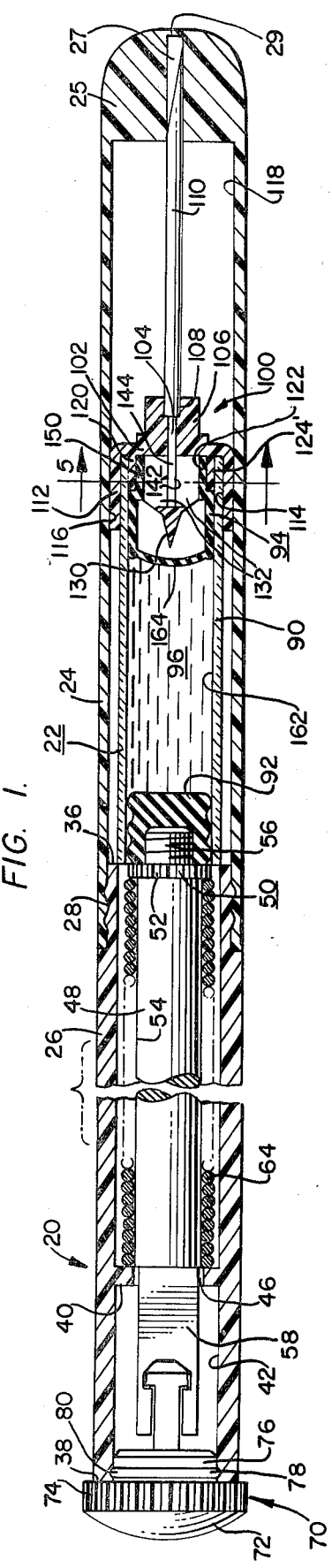

The self injector of this invention is spring power operated and as illustrated in the various figures of the drawings comprises a spring powered gun assembly 20 and a cartridge assembly 22 slidably carried within a cylindrical shield 24 affixed to the gun housing 26 by means of cooperating threads 28.

Specifically, the spring powered gun assembly 20 comprises a cylindrical housing 26 open at both its forward end 36 and its rearward end 38. A circular shoulder 40 extends radially inward from the inner surface 42 of the housing 26 to form an opening 46 of smaller diameter than that of the cylindrical gun housing 26. A circular plunger rod 48 is centrally positioned within gun housing 26 and is slightly shorter than the length of the housing. The plunger rod 48 has a head portion 50 including a flanged portion 52 forming an offset with respect to the outer surface 54 of the plunger rod 48. A threaded circular projection 56 extends forwardly from the flanged portion 52 and has a diameter substantially less than that of the flanged portion 52.

Figure 2:
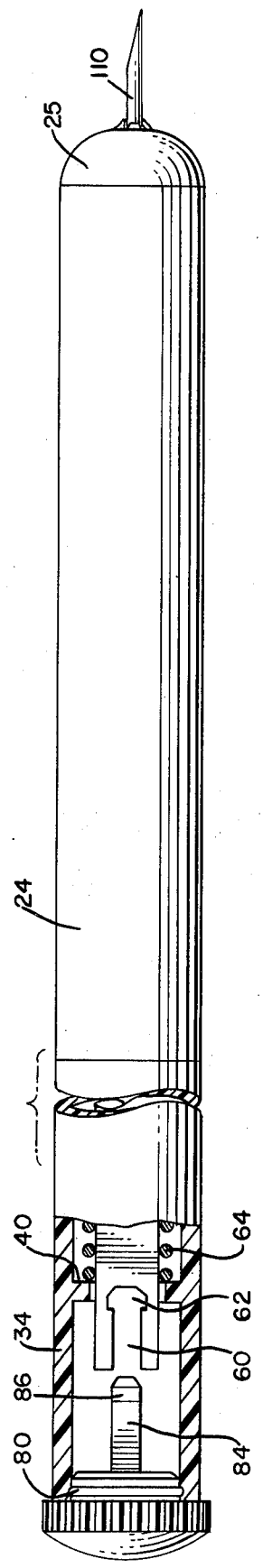
Figure 6:
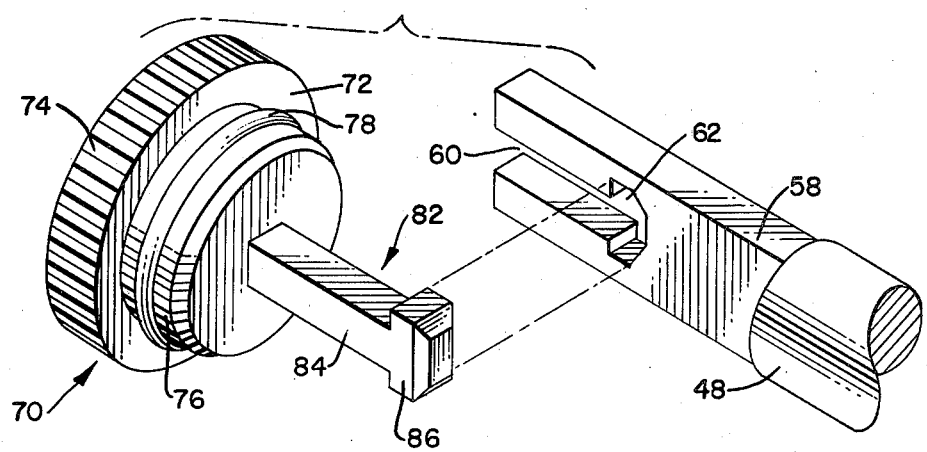

The rearward portion 58 of the plunger rod 48 is rectangular in cross section and terminates short of the rearward end 38 of the gun housing 26. Referring to FIGS. 2 and 6, a slot 60 is formed in the rearward portion 58 of the plunger rod 48 and terminates in an opening 62 somewhat larger than the slot 60 and having a truncated cone configuration wherein the portion of lesser size extends forwardly. A coil spring 64 fits over plunger rod 48 and is held in compressed condition between shoulder 40 and plunger rod flange 52.

In order to retain the plunger rod 48 in power ready condition, a release knob assembly 70 is provided for the rear end 38 of the housing 26. More particularly, the release knob assembly 70 includes a circular head 72 provided with serrations 74 to aid in gripping the head. A circular body portion 76 extends forwardly from head 72 and has a peripheral bead 78 midway its length. This bead 78 cooperates with groove 80 in the inner surface 42 of the gun housing 26 to retain the knob assembly 70 in assembled condition. A locking bar 82 extends forwardly from the body portion 76 and includes a bar portion 84 of square cross section terminating in a flat truncated cone-like locking element 86. Both the bar portion 84 and the locking element 86 are sized to operatively cooperate with slot 60 and opening 62 in plunger rod portion 58. The assembled position is illustrated in FIG. 1, while the perspective view is shown in FIG. 6.

The cylindrical cartridge shield 24 having a closed forward end 25 is threadedly connected to the gun housing 26 by means of cooperating threads 28 and slidably mounts a cartridge assembly 22. Said cartridge assembly 22 comprises a cylindrical tube 90 open at both its forward and rearward ends with plunger 92 slidably fitting within the tube at its rearward end to close same. A diaphragm 94 closes off the forward end of the tube 90 to form a medicament chamber 96 between the plunger 92 and the diaphragm 94. A nose piece 100 is fitted onto the forward end of tube 90 and includes a body portion 102 having a central bore 104 aligned with the longitudinal axis of tube 90. A circular projection 106 extends forwardly from the body 102 and has an opening 108 aligned with body bore 104. A cannula 110 is fitted into opening 108 of projection 106.

An outer cylindrical sleeve 112 extends rearwardly from body 102 with its longitudinal axis aligned with that of the body bore 104. Said outer sleeve 112 has an inner surface 114 and an outer surface 116 with the outer sleeve sized such that its outer surface 116 will slide smoothly within the inner surface 118 of the shield 24. An inner cylindrical sleeve 120 extends rearwardly from body 102 and has a diameter less than that of the outer sleeve 112 and is coaxial therewith. Said inner sleeve 120 has an inner surface 122 and an outer surface 124. The inner surface 114 of the outer sleeve 112 and the outer surface 124 of the inner sleeve 120 form an annular space to receive the forward end portion of cartridge tube 90.

Figure 4:
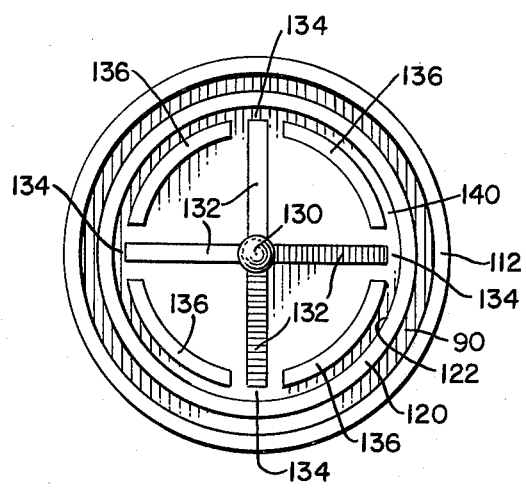
Figure 5:
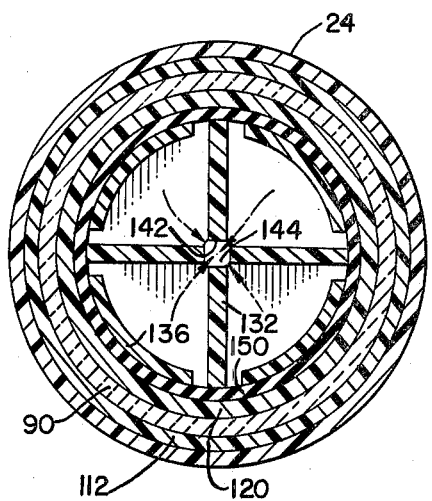

A spike 130 is positioned rearwardly of the nose piece body 102 and coaxial with the longitudinal axis of the outer sleeve 112. The spike 130 is conical in shape with its point directed rearwardly. Referring to FIGS. 1, 4 and 5, spike 130 is retained in position by means of four segmented supports 132 radially positioned at 90° intervals. Said supports are of equal size and extend rearwardly from the body 102 and connect to the base portion of spike 130 at which point they terminate. All supports extend radially outward and stop short of the inner surface 122 of the inner sleeve 120 to form a space 134. In order to further develop space 134 a plurality of segmented walls 136 may be provided so that with space 134 an annular space 140 is formed to receive a portion of the diaphragm 94. The segmented walls 136 extend from the base 102 rearwardly to a point short of the rearward ends of support 132. It should be noted that radially extending supports 132 on their inner radial ends 142 are spaced from the longitudinal axis of the nose piece bore 104 to form a connecting passageway 144.

The diaphragm 94 which closes off the forward end of the cartridge tube 90 comprises a cylindrical base 150 fitting into annular space 140 in the rearward side of the nose piece body 102 formed by segmented walls 136 and the inner face 122 of inner sleeve 120. The cylindrical base 150 has a forward end 152 and a rearward end 154 with a flange 156 extending radially outward from said rearward end and terminating in a diameter slightly less than that of the inner diameter of the cartridge tube 90. A cylindrical wall 160 extends rearwardly from the flange 156 and it too is sized to smoothly engage the inner wall 162 of the cartridge tube 90. A flexible diaphragm wall 164 extends across the rearward end of cylindrical wall 160 to provide the closing means for the forward end of the medicament chamber 96. The flexibility of the diaphragm wall 164 may be changed by varying the thickness of the wall as conditions dictate. It should be noted that the diaphragm wall 164 curves slightly outward toward the rear of the unit and is spaced from the point of the spike 130, see FIG. 1.

Figure 3:
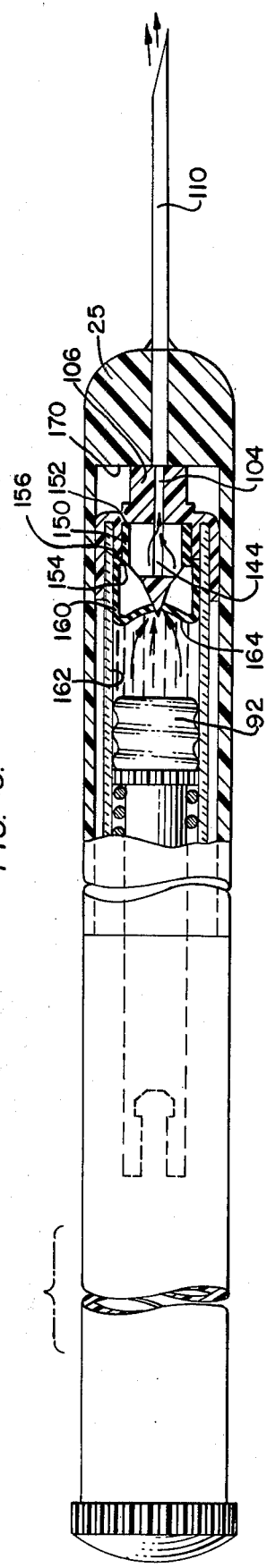

The operation and use of this self injector is quite simple, thus making it even more attractive for use by unskilled persons. The device ready for use is illustrated in FIG. 1 wherein the threaded projection 56 of plunger head 52 has been threadedly mated with the plunger 92 which is positioned in the rearward end of the cartridge tube 90. Further, the cartridge shield 24 is threadedly connected to gun housing 26 so that for all practical purposes the gun housing 26 and the cartridge shield 24 form a unitary housing. It should be noted that the cannula end of shield 24 includes a rather heavy solid end portion 25 provided with a hole 27 closed by a reduced thickness section 29. The end portion of the cannula 110 is slidably positioned in hole 27 with the end of the cannula spaced from section 29. The coil spring 64 is retained in compressed condition by means of locking bar 82 fitting into conformingly shaped slot 60 and opening 62 in plunger rod portion 58. When it is desired to inject the medicament which is in chamber 96, the shield end portion 25 is placed where the injection is to be made. After this, the release knob head 72 is rotated 90° either clockwise or counterclockwise whereby the locking element 86 has its thinner dimension aligned with the plunger rod slot 60 which is wider than the thickness of the locking element 86 consequently the plunger rod 48 is released, see FIG. 2, and the plunger rod 48 and cartridge assembly 22 move forward with the cannula 110 piercing the shield end portion 29. During this operation, the plunger rod 48 pushes the plunger 92 forward within the cartridge tube 90 thereby causing the cartridge to move forward and the medicament under pressure from the sliding plunger 92 to flex diaphragm cover 164 forwardly into engagement with the pointed end of spike 130. Continued movement of plunger 92 causes the diaphragm cover 164 to be pierced and allow medicament to flow out through cannula 110 into the injection locus (see FIG. 3). The movement of the cartridge slidably forward causes the nose piece projection 106 of the nose piece to abut against the rear face 170 of the front portion 25 of the shield 24. Further forward movement of the plunger 92 causes the medicament injection to be completed. The medicament flows from medicament chamber 96, past spike 130 into passageway 144 into body bore 104 and out through cannula 110. After injection the cannula is withdrawn to complete the injection procedure.

What is claimed is:

1. A self injector comprising in combination:
    a spring powered gun assembly, said assembly including a cylindrical housing, a plunger rod movably carried within said housing, spring means for actuating the plunger rod, and retaining means for holding the spring means in compressed position and upon actuation for releasing said spring means; and
    a cartridge assembly connected to the gun assembly, said cartridge assembly comprising a cylindrical shield connected to the gun housing, a cartridge slidably carried within the shield, said cartridge including a cylindrical tube, a plunger slidably mounted in the rearward end of said tube to close same off, a diaphragm positioned in the forward end of the tube to close off that end of the tube and form a medicament chamber between the plunger and the confronting face of the diaphragm, a nose piece fitted on the forward end portion of the tube, said nose piece having a body portion with a central bore therethrough and aligned with the longitudinal axis of the cartridge tube, the body portion having a forward and a rearward face, means extending forwardly from the nose piece body and in fluid communication with the aforesaid bore for receiving and mounting an injection cannula, means extending rearwardly from the nose piece body to receive the forward end of the cartridge tube, a spike distinct from any injection needle that might be mounted on the forward needle mounting means on the rearward side of the nose piece body with its point directed rearwardly, means for mounting the spike in the aforesaid position, and
    a diaphragm positioned in the forward end of the cartridge tube on the rearward side of the nose piece body, said diaphragm comprising a cylindrical body having a forward open end, a flexible and pierceable diaphragm portion closing off the rearward end, the diaphragm fits around and over the spike with the diaphragm closed end being spaced rearwardly of the spike point, whereby with the plunger rod aligned with the plunger firing of the gun will cause the plunger rod to move the plunger and force the medicament in the medicament chamber to flex the diaphragm and pierce same in the spike to establish flow from the medicament chamber to and through the cannula, said cartridge tube being simultaneously moved to insert the cannula in the prescribed locus.

2. The invention as set forth in claim 1 and wherein the nose piece and spike are unitary.

3. The invention as set forth in claim 1 and wherein the nose piece, spike and means for receiving and mounting the cannula are unitary.

4. The invention as set forth in claim 3 and wherein the spike is cone-shaped.

5. The invention as set forth in claim 1 and wherein the retaining means for holding the spring means in compressed position and upon actuation for releasing said spring means comprises a locking bar affixed to a knob rotatably carried in the rearward end of the gun housing, and a lock receiving opening in the rearward portion of the plunger rod into which the locking bar fits to retain the plunger rod in position for release.

6. The invention as set forth in claim 5 and wherein the locking bar comprises a rod of square cross section connected at one end of the knob and at the other to a lock member.

7. The invention as set forth in claim 6 and wherein the lock member is of truncated pyramid shape and functionally fits in an appropriately shaped portion of the lock receiving opening in the plunger rod.

8. A self injector comprising in combination:
   a spring powered gun assembly, said assembly including a cylindrical housing, open at its forward and rearward ends, a plunger rod movably carried within said housing, spring means for actuating the plunger rod, and retaining means for holding the spring means in compressed position and upon actuation for releasing said spring means; and
   a cartridge assembly connected to the gun assembly, said cartridge assembly comprising a cylindrical shield connected to the gun housing, a cartridge slidably carried within the shield, said cartridge including a cylindrical tube, a plunger slidably mounted in the rearward end of said tube to close same off, a diaphragm positioned in the forward end of the tube to close off that end of the tube and form a medicament chamber between the plunger and the confronting face of the diaphragm, a nose piece fitted on the forward end portion of the tube, said nose piece having a body portion with a central bore therethrough and aligned with the longitudinal axis of the cartridge tube, the body portion having a forward and a rearward face, means extending forwardly from the nose piece body and in fluid communication with the aforesaid bore for receiving and mounting an injection cannula, a cylindrical outer sleeve extending rearwardly from the body portion, a cylindrical inner sleeve extending rearwardly from said body portion and spaced radially inward from the outer sleeve, the inner and outer sleeves defining a space adapted to receive one end portion of the cylindrical tube, a spike centrally and axially positioned with respect to the outer sleeve with its point facing rearwardly, means for supporting the spike whereby fluid communication is provided between the spike and the cannula a diaphragm fitted within the rearward portion of the nose piece and comprising:

a cylindrical base having an upper and lower end, a flange extending radially outward from the upper end of the base, a cylindrical sleeve extending axially from the periphery of the flange in a rearward direction, and a flexible and pierceable member closing off the end of said cylindrical sleeve, said diaphragm being fitted within the nose piece so that the flexible and pierceable member is spaced rearwardly of the spike whereby with the plunger rod aligned with the plunger firing of the gun will cause the plunger rod to move the plunger and force the medicament in the medicament chamber to flex the diaphragm and pierce same in the spike to establish flow from the medicament chamber to and through the cannula, said cartridge tube being simultaneously moved to insert the cannula in the prescribed locus.

* * * * *